(12) United States Patent
Gauthier et al.

(10) Patent No.: US 7,550,156 B2
(45) Date of Patent: Jun. 23, 2009

(54) OPTIMISED PELLET FORMULATIONS

(75) Inventors: Francois Gauthier, Peymeinade (FR); Johan Tatin, Grasse (FR)

(73) Assignee: Rohm and Haas Company, Philadelphia, PA (US)

( * ) Notice: Subject to any disclaimer, the term of this patent is extended or adjusted under 35 U.S.C. 154(b) by 746 days.

(21) Appl. No.: 10/287,923

(22) Filed: Nov. 5, 2002

(65) Prior Publication Data
US 2003/0104072 A1    Jun. 5, 2003

(30) Foreign Application Priority Data
Nov. 23, 2001 (EP) .................. 01403015

(51) Int. Cl.
*A61K 9/14* (2006.01)
(52) U.S. Cl. ..................... 424/489
(58) Field of Classification Search .......... 510/298, 510/276, 349
See application file for complete search history.

(56) References Cited

U.S. PATENT DOCUMENTS

| | | | |
|---|---|---|---|
| 4,072,535 A * | 2/1978 | Short et al. .............. | 106/206.1 |
| 4,535,098 A * | 8/1985 | Evani et al. ................. | 521/149 |
| 4,590,227 A * | 5/1986 | Nakamura et al. .......... | 523/130 |
| 5,225,100 A * | 7/1993 | Fry et al. ................... | 510/298 |
| 5,830,543 A * | 11/1998 | Miyake et al. ............. | 428/35.2 |
| 6,221,832 B1 | 4/2001 | Casteel et al. .............. | 510/446 |
| 6,231,888 B1 | 5/2001 | Lerner | |
| 6,232,285 B1 | 5/2001 | Casteel et al. .............. | 510/446 |
| 6,254,892 B1 | 7/2001 | Duccini et al. | |
| 6,492,320 B2 | 12/2002 | Guo et al. ................... | 510/446 |
| 6,503,878 B1 | 1/2003 | Schwartz et al. ............ | 510/446 |
| 2003/0026835 A1 | 2/2003 | Nishii et al. | |

FOREIGN PATENT DOCUMENTS

| | | |
|---|---|---|
| EP | 0037026 A1 | 10/1981 |
| EP | 0075818 A | 4/1983 |
| EP | 0 481 547 A1 | 4/1992 |
| EP | 0 238 341 B2 | 12/1995 |
| EP | 0 522 766 B1 | 6/1997 |
| EP | 1 043 389 B1 | 5/2000 |
| EP | 1035196 A1 * | 9/2000 |
| EP | 0 799 886 B1 | 11/2002 |
| JP | 30198/87 | 2/1987 |
| JP | 264518/88 | 11/1988 |
| WO | WO 97/25979 | 7/1997 |
| WO | WO 00/44351 | 8/2000 |

* cited by examiner

*Primary Examiner*—M P Woodward
*Assistant Examiner*—Casey S Hagopian
(74) *Attorney, Agent, or Firm*—Carl P. Hemenway

(57) ABSTRACT

The invention concerns chemical compositions in the form of pellets which disintegrate quickly and efficiently in aqueous media. Such pellets comprise a) at least one constituent with pharmaceutical, agrochemical, water treatment, water softening, fabric softening or detergency activity; b) one or more disintegration agents comprising one or more cross-linked polyacrylate water absorbent polymers with a gel-formation time of 30 seconds or less and c) one or more water transport agents to transport water into the pellet when the pellet contacts water, wherein at least one of the said water transport agents comprises at least one starch or starch derivative.

5 Claims, No Drawings

OPTIMISED PELLET FORMULATIONS

The present invention relates to improved chemical compositions in pellet form which disintegrate quickly and efficiently in aqueous media. By "pellet", we mean any solid formulation, including, but not limited to, tablets, bricks, bars, granules, balls, or blocks, also agglomerated materials such as those which form as a result of material sticking together during storage, especially under high humidity conditions.

It is well known to use chemical compositions in pellet form, for example, in the field of medicine and agriculture and more recently other areas such as in detergent applications. Pellets offer certain advantages over granular compositions; they are non-dusting, do not require measuring, take less space because they are compressed and the ingredients do not segregate during transit and storage. However, problems are experienced regarding the dissolution or disintegration of the pellets in use. In the manufacturing process, a balance must be kept between a pellet pressure which is, on the one hand, high enough to ensure that the pellets are well formed and resistant to handling, and a pellet pressure which is, on the other hand, low enough to achieve an appropriate solubility/dispersibility profile. To combat this problem, the use of a processing additive either to improve pellet cohesion without the use of high pelleting pressure or to improve tablet dispersibility is known in the art.

Looking specifically at additives which improve dispersibility, Journal of Pharmaceutical Sciences Vol. 61, No., 11, 1972, pp 1695-1711 reviews the various classes of known disintegrants; for example, materials which, i) cause disintegration by evolving gas, such as sodium bicarbonate in the presence of citric or tartaric acid; ii) those which promote water absorption, such as starch, colloidal silicon dioxide, carboxymethyl cellulose and rice starch; iii) those which swell, for example, cross-linked polyacrylic acids, cross-linked gum arabic, carboxymethyl cellulose; iv) those which increase porosity such as potato and corn starch and finally v) those which undergo physicochemical bonding, such as micro crystalline cellulose and kaolin.

There are also many prior art patent documents directed to detergent tablets that contain disintegration agents. Examples of these include: EP-A-0 799 886 which discloses the use of starch derivatives, cellulose compounds, polyvinyl pyrrolidone compounds, polyvinyl pyrrolidone compounds, bentonite compounds, alginates, gelatine and pectines as disintegrants and EP-A-0 522 766 which lists corn, maize, rice and potato starches, and starch derivatives, cellulose and cellulose derivatives and various synthetic organic polymers such as polyethylene glycol, cross-linked polyvinyl pyrrolidine and inorganic materials which swell such as bentonite clay, as disintegrants.

EP-A-0 481 547 teaches multilayer machine dishwashing detergent tablets which contain an outer layer, a barrier layer and an inner layer. The tablets release the detergent ingredients sequentially, first from the outer layer and then from the inner layer and the time delay between the two dissolutions is controlled by the thickness and choice of ingredients in the barrier layer separating the outer and inner layers. One of the ingredients in this barrier layer is a disintegrant which preferably includes one of a maleic acid/acrylic acid copolymer or a salt thereof, ethylene maleic anhydride cross-linked polymer and polyethylene glycol.

EP-A-0 238 341 identifies sequestering agents, for instance, nitrilo triacetic acid or ethylene diamine tetra acetic acid or a low molecular weight anionic polymer formed from ethylenically unsaturated monomers e.g. unsaturated carboxylic acid, sulphonic acid or phosphonic acid monomers, as disintegrants. Further, this document mentions, when discussing the teaching of background art documents EP-A-0 075 818 and EP-A-0 037 026, that the conventional insoluble water swellable disintegration aids disclosed therein, such as high molecular carbohydrates like starch, pulverised cellulose such as ground wood, or polyvinyl pyrrolidone and so on, either do not lead to satisfactory disintegration or the disintegration is very slow at low temperatures. Another disadvantage observed through the use of cellulose and cellulose derivatives is that at use levels which are effective to promote disintegration, for example around 5% by weight of the tablet, the tablets are friable and break easily. This problem can be overcome by the addition of processing aids, for example binders that "glue" the tablet particles together, but this adds cost and reduces the volume of the tablet which is available for active ingredients. In addition these binders tend to slow down the disintegration of the tablet.

U.S. Pat. No. 6,232,285 describes disintegrating granules comprising water swellable cellulose derivatives associated with (meth)acrylic polymers/copolymers and gel forming or thickening surfactants. The (meth)acrylic polymer is in a form of a finely divided material, the blend being mixed prior compaction which results in orientation of anisotropic cellulose/cellulose derivatives. Examples are given in which linear or cross-linked polyacrylates have Molecular Weights from 40,000 to 2 million.

U.S. Pat. No. 6,221,832 relates to disintegrating granules with similar composition to those above, in which starch and starch derivatives are used in partial substitution of cellulosic materials, and associated with finely divided copolymers of (meth)acrylic acid and surfactants. Cold-swelling or cold-soluble starches are preferably used, such as polygalactomannanes. Starch derivatives are preferably used if the original material does not swell in cold water. Formulations given as examples show high amounts of cellulosic material, from 48 to 85% by weight of the disintegrating granule, and low levels of starch derivatives, for example, about 10% by weight of the disintegrating granule, in association with fatty alcohol surfactants.

The dissolution or disintegration of tablets for use in detergent compositions for automatic dishwashing is usually controlled to ensure dissolution which is regular but not too quick so as to avoid too much of the detergent composition being consumed in the pre-wash. However, during the main dishwash cycle it is advantageous for the remainder of the tablet to dissolve quickly so that residual tablet solids are not a problem on the dishware. By contrast, a key requirement in detergent compositions for laundry applications is to deliver as much of the detergent composition as possible so that it is available in the initial step of the wash. This will also be the case if the dishwashing machine has no pre-wash cycle. Since calcium and magnesium hardness ions in the wash water are already present at the beginning of the wash cycle, there is a high risk that sequestering ingredients are at too low a concentration and these will precipitate together with these hardness ions. This will result in insoluble scale being formed on the garments being laundered and a reduced amount of active material in the detergent composition being available for cleaning. With certain builders in detergent compositions, for example, sodium tripolyphosphate (STPP), this problem is critical since Ca/STPP precipitates can form scale that is very difficult to remove. The size of the tablets and the application conditions will also affect the tablet dispersability profile; for example, tablets for use in laundry applications are typically considerably larger than those used in automatic dishwashing machines or in water treatment; 40 g up to 55 g tablets for laundry versus 20-25 g tablets for dishwashing and water softening. This fact, coupled with the tendency for the laundry tablet to be buried in the garments being washed means that the solubility requirements are particularly difficult to meet for tablets used in laundry applications as compared to other applications.

The applicants have previously disclosed, in French patent application 9807643, pellet formulations which disintegrate or dissolve very quickly on contact with water, making them suitable for use in applications which require the active ingredients to be delivered quickly. These pellets comprise: a) at least one constituent with pharmaceutical, agrochemical, water treatment, water softening, fabric softening or detergency activity; and b) at least one disintegration agent comprising one or more cross-linked polyacrylate water absorbent polymers with a gel-formation time of 30 seconds or less.

Such pellets have sufficient strength so that they do not crumble or break whilst being stored, transported or handled and are able to be stored under various climatic conditions involving fluctuating temperatures and humidities. It is particularly desirable that the pellets are sensitive to water but not to moisture. They must also have good activity, which requires a high content of active ingredients, and be able to exert this good activity at different temperatures and over a wide spectrum of application conditions, for example over a range of degrees of water hardness in the case of detergents.

French Patent Application 9902791 describes ways to improve further the rate of disintegration. It has been observed by the applicants that the rate of pellet disintegration is increased with increasing levels of disintegration agent present the pellet. However, when the pellet contains these disintegration agents in amounts of 2% or more by weight, a gel forms when the pellet comes into contact with water, and this prevents penetration of the water into the centre of the tablet, i.e. this gel decreases the rate of disintegration. This problem can be solved by combining lower levels of cross-linked polyacrylate with water transport agents such as cellulosic materials, especially amorphous or microcrystalline types with a particle size of 200 µm or less.

The aim of the present invention, therefore, is to provide pellet formulations which have still further improved rates of disintegration and which also overcome the difficulties caused by gel formation.

The applicants have now found that starch and starch derivatives can advantageously be used as water transport agents such that when combined with low levels of disintegration agent in the pellet they can surprisingly and unexpectedly provide high disintegration performances. Furthermore, the applicants have also found that the process used to combine the water transport agent and the disintegration agent together, has a profound effect on the rate of disintegration of the final pellet.

Accordingly, the present invention provides a chemical composition in pellet form comprising: a) at least one constituent with pharmaceutical, agrochemical, water treatment, water softening, fabric softening or detergency activity; b) one or more disintegration agents comprising one or more cross-linked polyacrylate water absorbent polymers with a gel-formation time of 30 seconds or less; and c) one or more water transport agents to transport water into the pellet when the pellet contacts water, wherein at least one of the said water transport agents comprises at least one starch or starch derivative.

The purpose of the water transport agent(s) is to entrain water quickly into the centre of the pellet so that the cross-linked polyacrylate water absorbent polymer(s) within the pellet can be caused to swell, thereby facilitating fast disintegration of the pellet. Without such water transport agent(s) the water absorbent polymer close to the surface of the pellet will swell on contact with water and, if the polymers are at a concentration of 2% or more by weight of the pellet, they will form a gel that will effectively prevent further water penetration into the pellet.

The total amount of water transport agents in the pellet composition is at least 0.5% by weight, and preferably at least 2.0% by weight. At least one of the water transport agents comprise at least one starch or starch derivative and it is preferred that the one or more water transport agents comprise at least 20%, more preferably at least 50%, in weight (dry/dry) of one or more of starch and starch derivative. Advantageously, the water transport agents contain at least 80% in weight (dry/dry) of at least one starch or starch derivative. Such percentage can notably be of 100% by weight (dry/dry). A medium to large particle size for the water transport agents is advantageous, for example, 200 µm to 1200 µm and preferably 200 to 600 µm.

The total amount of cross-linked polyacrylate water absorbent polymer (disintegration agent) is generally from 0.1 to 2.0% by weight of the pellet formulation, and preferably from 0.25 to 0.75% by weight. A particularly favourable composition comprises 0.5% by weight of the pellet of cross-linked polyacrylate water absorbent polymer and 2.5% by weight of the pellet of starch and starch derivative.

It is particularly advantageous for the cross-linked polyacrylate water absorbent polymers to have a gel-formation time of 30 seconds or less, most preferably 10 seconds or less.

In a further embodiment, the present invention is also directed to a method of improving the speed of disintegration of chemical compositions in pellet form comprising the step of incorporating together:

a) at least one constituent with pharmaceutical, agrochemical, water treatment, water softening, fabric softening or detergency activity;

b) one or more disintegration agents comprising one or more cross linked polyacrylate water absorbent polymers with a gel formation time of 30 seconds or less; and c) one or more water transport agents to transport water into the pellet when the pellet contacts water, wherein at least one of the said water transport agents comprises at least one starch or starch derivative.

By "improving the speed of disintegration", it is meant that the time of disintegration is less for pellets according to the present invention as compared with pellets which do not contain a mixture of one or more cross linked polyacrylate water absorbent polymers with a gel formation time of 30 seconds or less and one or more one water transport agents that comprise at least one starch or starch derivative.

The one or more water transport agents and the one or more cross-linked polyacrylate water absorbent polymers (disintegration agent) may be simply mixed with the at least one constituent with pharmaceutical, agrochemical, water treatment, water softening, fabric softening or detergency activity (component (a) described above) before compacting to form pellets, or, alternatively, the one or more water transport agents and the one or more cross-linked polyacrylate water absorbent polymers may be cogranulated, either in the presence or absence of the component (a), to form disingetrating granules, and these can then compacted to form pellets.

The present invention, therefore, also provides a process of combining one or more disintegration agents comprising one or more cross-linked polyacrylate water absorbent polymers with a gel-formation time of 30 seconds or less with one or more water transport agents comprising at least one starch or starch derivative to produce disintegrating granules, comprising the step of cogranulating the one or more disintegration agents with the one or more water transport agents, optionally in the presence of the at least one constituent with pharmaceutical, agrochemical, water treatment, water softening or detergency activity.

Such disintegrating granules are preferably manufactured according to a "wet granulation process", in which any known granulation technique is applied in the presence of water, and/or any other liquid phase or liquefied phase. This process usually implies a first step in which all components are dry-blended, at moderate temperature and low (ambient) pressure.

This technique differs from processes where the different components are simply dry mixed, and eventually compacted without requiring an additive to ensure granulation, because granulation ensures that all components are homogeneously distributed in the final granules containing the said components. It also differs from techniques involving steaming or drying drum, extrusion or spray drying, in which the blend is encountering high temperature conditions.

A suitable process to produce disintegration granules that markedly increase the rate of disintegration of the pellet involves modifying the disintegration agent by spraying it with water prior to incorporating it into the pellet. The quantity of water may be from 5-50% w/w and is preferably from 5-20% w/w. Such spray of water can be carried out during the cogranulation process of the ingredients in order to help the agglomeration of starch materials with cross linked polyacrylates.

The cross-linked polyacrylate water absorbent polymers used in the present invention are typically those resulting from the radical polymerizations and cross-linking of, at least one water soluble ethylenically unsaturated monomer selected from: (meth)acrylic acid, alkali metal or ammonium salts of (meth)acrylic acid, (meth)acrylic acid esters, maleic acid, maleic anhydride and (meth)acrylamide. Relatively high degrees of cross-linking are necessary to obtain a short gel formation time as mentioned here above. Under these conditions the polyacrylate particle tends to be water insoluble and the Molecular Weight is considerably higher than 2 million; indeed, the molecular weight is so high that the real definition of Mw is not applicable to these fast swelling polyacrylates, and it can no longer be measured under classical chromatography techniques.

The cross-linking reaction may be carried out using at least one of the following three methods:

i) Cross-linking by radical polymerisation with a co-monomer comprising at least two double bonds. Examples of such co-monomers include: trimethylol propane di(tri) (meth) acrylate, N,N-methylene bis(methyl)acrylamide, glyoxal bis acrylamide, ethylene glycol di(meth)acrylate;

ii) Cross-linking by radical copolymerisation with a so-called functional monomer comprising one double bond (active in copolymerisation) and, at least one functional group capable of leading to cross-linking reactions between a functional group and a chemically active moiety of the main water soluble monomer(s). Examples of this type of cross-linker include: N-methylol(meth)acrylamide, and glycidyl(meth)acrylate; and iii) Cross-linking by adding a non-polymerisable functional cross-linker containing at least two functional groups capable of reacting with the chemically active moieties of the water soluble monomer(s). Examples of this type of cross-linker include: glyoxal, ethylene glycol, (poly)ethylene glycol diglycidyl ether, (poly)propylene glycol diglycidyl ether, (di)glycerol polyglycidyl ether, polyglycerol polyglycidyl ether, epichlorohydrin, ethylene di-amine and zinc acetate.

The amount of cross-linker necessary for the production of the water-absorbing polymers is typically in the range of 0.001 and 10 weight percent, most preferably in the range of 0.01 and 5 weight percent, based upon the total weight of water-soluble ethylenic unsaturated monomer(s).

The cross-linked polyacrylate water absorbent polymers used in the present invention may be produced by any suitable radical polymerisation method. The solution-type polymerisation processes (also called gel processes) most commonly employed are those disclosed in EP-A-0 530 438, and a typical reversed-phase suspension polymerisation process is such as that described in EP-A-0 258 120. Preferably, the cross-linked polyacrylate water absorbent polymers used in the present invention have a gel-formation time of less than 10 seconds.

In addition to the composition comprising at least one constituent with pharmaceutical, agrochemical, water treatment, water softening, fabric softening or detergency activity, the composition may also comprise other ingredients including, for example, one or more of the following: processing additives, adjuvants, coatings materials, enzymes, builders, scale inhibitors, emulsifiers, surfactants, soaps, dispersants, zeolites, de-greasing agents, anti-foaming agents, phosphates, phosphonates, zeolites, carbonates, bicarbonates, citrate, citric acid, organic chelants, bleach, optical brighteners, fillers, extenders, soil removers, deflocculating agents, anti-coagulants, anti-drift agents, diluents, and carriers.

The present invention will now be described with reference to the following Examples.

The test procedures used are intended to simulate a real application. Detergent tablets using a typical laundry detergent composition were made using conventional tablet making equipment. Test tablets were loaded with both a disintegration agent and a water transport agent, and the disintegration efficiency of these test tablets was then tested and compared against similar control tablets loaded with either, only a disintegration agent, or only a water transportation agent or without either a disintegration agent or a water transport agent. The laundry detergent composition used is detailed in Table 1 below:

TABLE 1

| Ingredients | Detergent Composition |
|---|---|
| Anionic Surfactant | 5-15% |
| Non-ionic Surfactant | 5-15% |
| Soap | <5% |
| Zeolite | >30% |
| polymer builder | <5% |
| Phosphonate | <5% |
| Bleach | 5-15% |

The disintegration agents tested are cross-linked polyacrylate water absorbent polymers with a gel formation time of about 5 seconds. These materials are available from Rohm and Haas Company, under trade names Acusol 771® and Acusol 772®.

The gel formation time of the disintegration agent was measured using the following method, often referred to in the art as the vortex test or vortex swelling rate test.

An aqueous solution of sodium chloride is prepared by dissolving analytical grade sodium chloride in demineralised water up to a 0.9% weight concentration of salt in the final solution. This 0.9% wt. sodium chloride aqueous solution is a reference test liquid ("test liquid") commonly used in the characterisation of water absorbing polymers. In a temperature controlled room (20° C.), the cross-linked polyacrylate water absorbing polymer (2 g) is introduced into a beaker (100 ml) of internal diameter 55 mm. The beaker is placed over an electromagnetic stirrer and a magnetic bar (45 mm×8 mm) is introduced into it for stirring. The stirring speed is fixed at 600+/−20 rpm and the beaker is rapidly charged with the test liquid (50 g). As soon as addition of the test liquid is complete, this is counted as time zero and the point from which time is measured. Time measurements are stopped when the stirring vortex has disappeared due to the formation of a gel by the water-absorbing polymer. For extremely fast gelling polymers, it may be necessary to invert the order of addition of the polymer and test liquid to the beaker.

The rate of disintegration of the test and control tablets was determined using the following test method.

Test and control tablets containing the detergent composition given in Table 1 were prepared using conventional tablet making apparatus. A measure of the rate of disintegration for each tablet was measured as follows. A pre-weighed tablet was placed on a support in a 5 liter beaker filled with cold tap water (4.5 liters) at a temperature of 16-17° C. The solution was then agitated at 400 rpm for 10 minutes using a magnetic bar and magnetic bar stirring apparatus. At the end of the test cycle, the residue was placed in a cup, oven dried at 80° C. for 2 hours and re-weighed. The percentage residue was calculated as follows:

$$\frac{\text{Weight of residue} \times 100}{\text{Weight of tablet at the start}}$$

The results of the tests are presented in Table 2 below:

TABLE 2

Percentage of tablet remaining.

| Example | Additive | % Residue after 10 mins | Comments |
|---|---|---|---|
| 1 | None (control) | 88 | Tablet difficult to dissolve |
| 2 | 0.5% Disintegration agent (control) | 70 | Tablet difficult to dissolve |
| 3 | 1.5% Disintegration agent (control) | 63 | Tablet difficult to dissolve |
| 4 | 2% Amorphous cellulose (control) | 51 | Moderate rate of disintegration |
| 5 | 2% Native Corn Starch (control) | 41 | Moderate rate of disintegration |
| 6 | 1% Disintegration agent + 2% Amorphous cellulose (prior art) | 39 | Moderate rate of disintegration |
| 7 | 0.5% Disintegration agent + 2% Native Corn Starch | 32 | Good rate of disintegration |
| 8 | 1% Disintegration agent + 2% Native Corn Starch | 24 | Good rate of disintegration |

| Example | Additive (granulate form) | % Residue after 10 mins | Comments |
|---|---|---|---|
| 9 | 5% Granule T-484 | 30 | Nice tablet, and good rate of disintegration |
| 10 | 5% Granule T-485 | 5 | Nice tablet, and excellent rate of disintegration |
| 11 | 3% Granule T-489 | 12 | Nice tablet, and excellent rate of disintegration |

Granules T-484 and T-485 are cogranules composed, in weight (dry/dry), of 10% cross-linked polyacrylate and 90% of starchy compositions conceived and manufactured by ROQUETTE FRERES (France), the said starchy compositions containing about 90% in weight (dry/dry) of a wheat starch and about 10% in weight (dry/dry) of, respectively, a pregelatinized waxy corn starch (granules T-484) or a crosslinked potato starch (granules T-485), the granules being further agglomerated. Granule T-489 is based, in weight (dry/dry), on 16.7% cross-linked polyacrylate+83.3% of the same starchy composition of ROQUETTE as used above for granules T-485, the granules being further agglomerated.

As demonstrated by these results, tablets comprising a combination of a disintegration and a starch-containing water transport agent, Examples 7 to 11, produce excellent tablets and disintegrate much quicker than tablets which only comprise one of these two ingredients. Examples 9 to 11 show that such a combination, agglomerated into a granulated form, provides considerable improvement in the rate of disintegration of the tablet.

The invention claimed is:

1. Chemical composition in pellet form comprising:
  a) at least one constituent with pharmaceutical, agrochemical, water treatment, water softening, fabric softening or detergency activity;
  b) 0.25% to 0.75% by weight of the pellet, one or more cross-linked polyacrylate water absorbent polymer with a gel-formation time of 30 seconds or less; and
  c) at least 2% by weight of the pellet, one or more starch or starch derivative.

2. Chemical composition according to claim 1 wherein the one or more cross-linked polyacrylate water absorbent polymers are treated with water prior to formation of the pellet.

3. A method of making the composition of claim 1 comprising the step of cogranulating said one or more cross-linked polyacrylate water absorbent polymer with a gel-formation time of 30 seconds or less with said one or more starch or starch derivative, optionally in the presence of the at least one constituent with pharmaccutical, agrochemical, water treatment, water softening or detergency activity.

4. Process according to claim 3 wherein the cogranulation step involves a wet granulation process.

5. Chemical composition according to claim 1 wherein the one or more cross-linked polyacrylate water absorbent polymer has a gel-formation time of 10 seconds or less.

* * * * *